(12) United States Patent
Hartle et al.

(10) Patent No.: US 8,871,514 B2
(45) Date of Patent: Oct. 28, 2014

(54) METHODS OF PREPARING NUTRITIVE MEDIA FOR GROWTH AND/OR GERMINATION OF PLANT EMBRYOS

(75) Inventors: Jeffrey E. Hartle, Tacoma, WA (US); William C. Carlson, Olympia, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 634 days.

(21) Appl. No.: 12/874,089

(22) Filed: Sep. 1, 2010

(65) Prior Publication Data

US 2011/0076772 A1    Mar. 31, 2011

Related U.S. Application Data

(60) Provisional application No. 61/247,364, filed on Sep. 30, 2009.

(51) Int. Cl.
*C12N 5/00* (2006.01)
*C12N 5/02* (2006.01)
*C12N 5/04* (2006.01)

(52) U.S. Cl.
CPC ........................................ *C12N 5/04* (2013.01)
USPC ........... 435/430; 435/410; 435/420; 435/422; 435/431

(58) Field of Classification Search
USPC .......................... 435/410, 420, 422, 430, 431
See application file for complete search history.

(56) References Cited

U.S. PATENT DOCUMENTS

| 2,671,985 | A | 3/1954 | Vogelsang |
| 2003/0167684 | A1* | 9/2003 | Carlson et al. ................ 47/57.6 |
| 2005/0108936 | A1 | 5/2005 | Hartle et al. |
| 2005/0150161 | A1 | 7/2005 | Hartle et al. |
| 2007/0283621 | A1 | 12/2007 | Holloway |

FOREIGN PATENT DOCUMENTS

| EP | 373348 A2 | 6/1990 |
| WO | 9926470 A1 | 6/1999 |

OTHER PUBLICATIONS

Van Winkle et al. "The combined impact of pH and activated carbon on the elemental composition of a liquid conifer embryogenic tissue initiation medium," Plant Cell Rep (2003) 22:303-311.*
Thomas, T.D. "The role of activated charcoal in plant tissue culture," Biotechnology Advances 26 (2008) 618-631.*
Johansson et al. "Correlations between activated charcoal, Fe-EDTA and other organic media ingredients in cultured anthers of *Anemone canadensis*," Physiologia Plantarum 80: 243-249, 1990.*
Thomas, T.D., "The role of activated charcoal in plant tissue culture," Biotechnology Advances 26 (2008) 618-6310.*
Van Winkle et al. ("The combined impact of pH and activated carbon on the elemental composition of a liquid conifer embryogenic tissue initiation medium," Plant Cell Rep (2003) 22:303-311.*
Thomas, Dennis T., "The role of activated charcoal in plant tissue culture," Biotechnology Advances 26 (2008) 618-631, Aug. 22, 2008.

* cited by examiner

*Primary Examiner* — Susan McCormick Ewoldt
(74) *Attorney, Agent, or Firm* — Baker & Hostetler LLP

(57) ABSTRACT

In one aspect, a method is provided for producing an improved nutritive medium comprising an adsorbent material for culturing plant embryos.

18 Claims, 1 Drawing Sheet

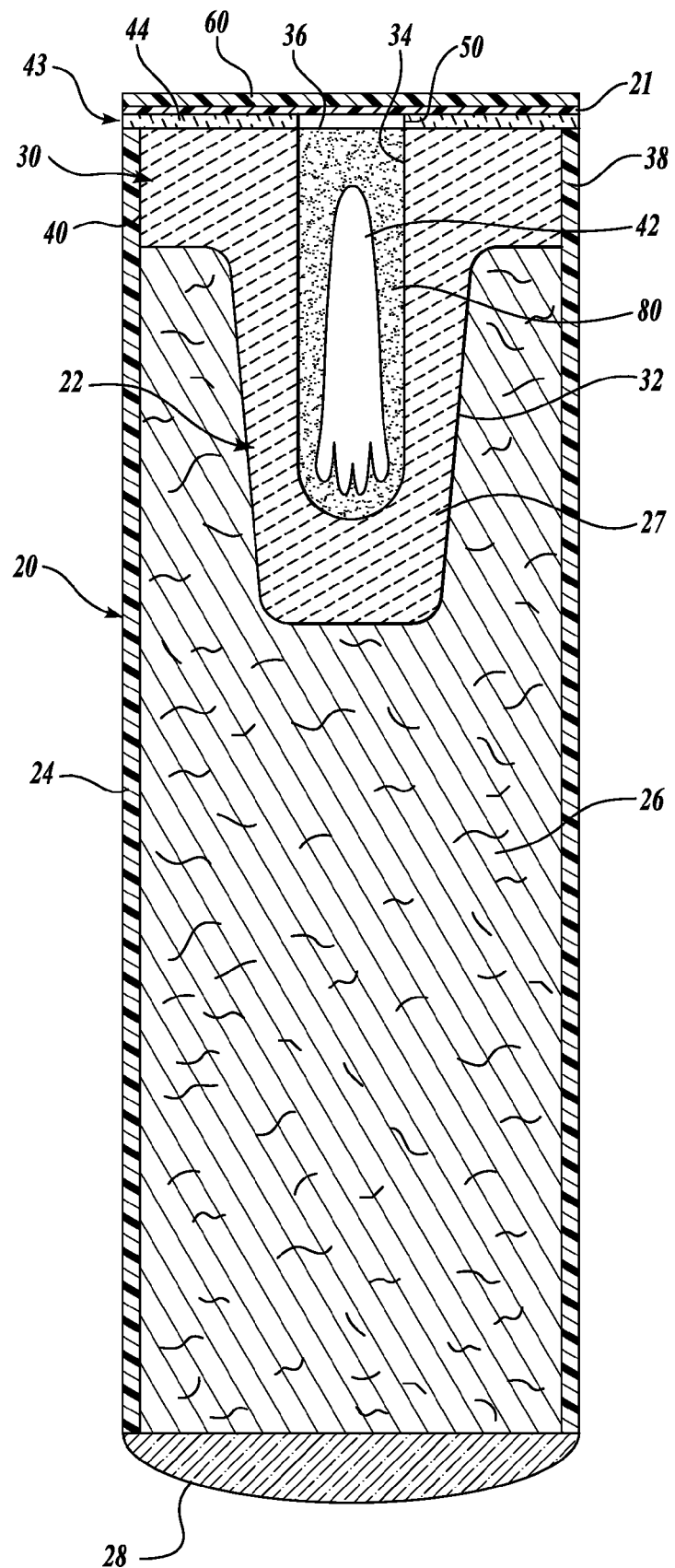

ical process in that they are capable of germinating to form a plant. Somatic embryos of gymnosperms, such as conifers, reach the cotyledonary stage of development at the end of the development phase.

METHODS OF PREPARING NUTRITIVE MEDIA FOR GROWTH AND/OR GERMINATION OF PLANT EMBRYOS

CROSS-REFERENCE TO RELATED APPLICATION

This application is entitled to and claims the benefit of priority under 35 U.S.C. §119 from U.S. Provisional Patent Application Ser. No. 61/247,364 filed Sep. 30, 2009, and titled "METHODS OF PREPARING NUTRITIVE MEDIA FOR GROWTH AND/OR GERMINATION OF PLANT EMBRYOS," the contents of which are incorporated herein by reference.

FIELD OF THE INVENTION

The present invention relates to methods for producing improved nutritive media for growth and/or germination of plant embryos.

BACKGROUND

It is often desirable to plant large numbers of genetically identical plants that have been selected to have advantageous properties, but in many cases it is not feasible to produce such plants using standard breeding techniques. In vitro culture of somatic or zygotic plant embryos can be used to produce large numbers of genetically identical embryos that have the capacity to develop into normal plants. However, the resulting embryos lack the protective and nutritive structures found in natural botanic seeds that shelter the plant embryo inside the seed from the harsh soil environment and nurture the embryo during the critical stages of sowing and germination. Attempts have been made to provide such protective and nutritive structures by using manufactured seeds, but so far germination from manufactured seeds is less successful than from natural seeds. There remain large differences between manufactured seeds and corresponding natural seeds. Whereas, the embryo relies on the megagametophyte for nutrients useful for germination, the embryo in a manufactured seed relies on the nutritive medium that is provided in the manufactured seed.

Therefore, there is a need for generating improved nutritive medium that is useful for improving rates of conversion for manufactured seeds containing somatic embryos to provide a large number of normal germinants. The present invention addresses this and other needs.

SUMMARY

In accordance with one aspect of the invention, a method is provided for producing an improved nutritive medium comprising an adsorbent material for culturing plant cells. The method in accordance with this aspect of the invention comprises (a) determining whether there is a decrease in the concentration of one or more components in a first nutritive media after incubation with a desired amount of adsorbent material; and (b) producing an improved nutritive medium comprising the same components as the first nutritive medium, wherein the improved nutritive medium comprises: (i) an increased concentration of the one or more components that was determined in step (a) to decrease in concentration in the presence of the absorbent material; and (ii) the same type of absorbent material at a concentration range within two-fold of that which was used in accordance with step (a).

In accordance with another aspect of the invention, a method is provided for producing an improved nutritive medium comprising an adsorbent material for culturing plant cells. The method in accordance with this aspect of the invention comprises: (a) incubating a first nutritive media comprising a pre-determined initial concentration of components comprising one or more carbon sources, vitamins, minerals and amino acids with a desired amount of adsorbent material to be added to an improved nutritive media; (b) determining whether there is a decrease in the concentration of one or more of the components in the first nutritive media after the incubation according to step (a) as compared to the pre-determined initial concentration of the component; and (c) producing an improved nutritive medium comprising the same components as the first nutritive medium, wherein the improved nutritive medium comprises: (i) an increased concentration of the one or more components that was determined in step (b) to decrease in concentration in the presence of the absorbent material; and (ii) the same type of absorbent material at a concentration range within two-fold of that which was used in accordance with step (a).

The methods of making an improved nutritive medium and are useful for the growth and/or germination of a plant embryo, such as a conifer embryo.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a side cross-sectional planar view of an exemplary manufactured seed comprising a plant embryo in accordance with various embodiments of the invention.

DETAILED DESCRIPTION

The present disclosure provides manufactured seeds comprising a modified nutritive medium that results in improved germination frequency in comparison to manufactured seeds comprising standard nutritive medium containing nutrient-treated charcoal.

As used herein, "a plant somatic embryo" refers to an embryo produced by culturing totipotent plant cells such as meristematic tissue under laboratory conditions in which the cells comprising the tissue are separated from one another and urged to develop into minute complete embryos. Alternatively, somatic embryos can be produced by inducing "cleavage polyembryogeny" of zygotic embryos. Methods for producing plant somatic embryos suitable for use in the methods of the invention are standard in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation medium that includes hormones to initiate the formation of embryogenic cells, such as embryonic suspensor masses that are capable of developing into somatic embryos. The embryogenic cells may then be further cultured in a maintenance medium that promotes establishment and multiplication of the embryogenic cells. Subsequently, the multiplied embryogenic cells may be cultured in a development medium that promotes the development of somatic embryos, which may further be subjected to post-development treatments such as cold treatments. The somatic embryos used in the methods of the invention have completed the development stage of the somatic embryogenesis process. They may also have been subjected to one or more post-development treatments.

Typically, the plant somatic embryos used in the invention have a shoot end and a root end. In some species of plants, the shoot end includes one or more cotyledons (leaf-like structures) at some stage of development. Plant embryos suitable for use in the methods of the invention may be embryos from any plant species, such as dicotyledonous or monocotyledonous plants or gymnosperms, such as conifer zygotic or somatic embryos (i.e., pine, such as Loblolly pine, fir, or Douglas-fir). For use in manufactured seeds according to the present invention, the plant embryo is developed sufficiently to have a shoot end and a radicle end. In certain species of plants, the shoot end includes one or more cotyledons in some stage of development. In other types of plants, the cotyledon(s) are situated in locations other than the shoot end.

As used herein, the term "germination" refers to a physiological process that results in the elongation of a plant embryo along its axis and is complete when the embryo has elongated to the point of protrusion through the seed coat or manufactured seed lid.

As used herein, the term "complete germination" refers to a manufactured seed having root protrusion through the seed coat or manufactured seed lid.

A manufactured seed for use in the invention comprises a plant embryo, a manufactured seed coat, and a nutritive medium. FIG. 1 is a side cross-sectional planar view of an exemplary manufactured seed 20 comprising a plant embryo 42 disposed within. As shown in FIG. 1, the embryo 42 is disposed within a cavity 34, is in functional contact with nutritive media 26 and is suitably sealed therein by a live end seal 43. It will be understood that FIG. 1 provides a representative embodiment of a manufactured seed 20 comprising a plant embryo, a manufactured seed coat enclosing the plant somatic embryo comprising an orifice, nutritive media in functional contact with the plant embryo, and a lid sealing the plant somatic embryo within the manufactured seed; however, the method is not limited to the particular embodiment of the manufactured seed shown in FIG. 1. In the exemplary embodiment shown in FIG. 1, the manufactured seed 20 comprises a seed coat 24, nutritive media 26, a dead end seal 28, and an optional cylcap 22 (shoot restraint). In the exemplary embodiment shown in FIG. 1, the manufactured seed 20 comprises a plant embryo 42, a seed coat 24, nutritive media 26 in functional contact with the plant embryo and an optional cylcap 22 (shoot restraint).

As used herein, a "manufactured seed coat" refers to a structure analogous to a natural seed coat that protects the plant embryo and other internal structures of the manufactured seed from mechanical damage, desiccation, from attack by microbes, fungi, insects, nematodes, birds, and other pathogens, herbivores, and pests, among other functions. The seed coat 24 may be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are generally non-toxic and provide a degree of rigidity. The seed coat can be biodegradable, although typically the seed coat remains intact and resistant to penetration by plant pathogens until after emergence of the germinating embryo. The seed coat may be formed from a section of tubular material. The seed coat may be a sectioned straw of fibrous material, such as paper. The sections of straw may be pretreated in a suitable coating material, such as wax. Alternatively, the seed coat may be formed from a tubular section of biodegradable, plastic material. One such material is polylactic acid ("PLA") and is sold by MAT-UR of Los Angeles, Calif. Another suitable material is a polycaprolactone ("PCL") mixture, such as CAPA 6800 (Perstorp polyols Inc., Toledo, Okla. 43612) with or without a 1% Tegomer H SI6440 plasticizer (Degussa Goldschmidt Chemical Corp, 914 East Randolph Road, Hopewell, Va. 23860). Such biodegradable plastic tubes may or may not require a wax coating, as such tubes are already resistive to environmental elements. Additives such as antibiotics and plant-growth regulators may be added to the seed coat, for example, by incorporation into the material forming one or more of the layers of the seed coat or by coating or otherwise treating the layer(s) with the additive by conventional means.

The cylcap 22, also known as a shoot restraint, or cotyledon restraint, is suitably manufactured from a porous material having a hardness strong enough to resist puncture or fracture by a germinating embryo, such as a ceramic or porcelain material, and includes an end seal portion 30 and a cotyledon restraint portion 32. The restraint portion 32 has an interior surface for contacting and surrounding at least the shoot end of a plant embryo and resists penetration by the shoot end during germination. The shoot restraint prevents the shoot end of the embryo, such as the cotyledons, from growing into and becoming entrapped in the nutritive medium (also referred to as gametophyte medium). The cotyledon restraint portion 32 is suitably integrally or unitarily formed with the end seal portion 30. The cylcap 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo 42 therein. As shown in FIG. 1, the cylcap 22 comprises a plurality of pores 27, wherein the pores 27 allow the nutritive media 26 access into the inside of the cavity 34 comprising the embryo 42, and therefore allows the nutritive media 26 to functionally contact the embryo 42 under conditions sufficient to generate a conditioned embryo, as described herein.

The restraint is porous to allow access of the embryo to water, nutrients, and oxygen. The shoot restraint may be fabricated from any suitable material, including, but not limited to, glassy, metal, elastomeric, ceramic, clay, plaster, cement, starchy, putty-like, synthetic polymeric, natural polymeric, and adhesive materials. Exemplary shoot restraints are described in U.S. Pat. No. 5,687,504 (e.g., Col. 3, line 61, to Col. 4, line 13; Col. 18, line 7, to Col. 22, line 2), herein incorporated by reference.

As further shown in FIG. 1, in some embodiments of the manufactured seed 20, fill material 80 either completely or partially surrounds the embryo 42 and increases the surface area of the embryo 42 in functional contact with the nutritive media 26, thereby providing multiple pathways for the nutrients from the nutritive media 26 to pass to the embryo 42. Although it is preferred that the fill material 80 substantially centers the embryo 42 within the cavity 34, the embryo 42 need not be so positioned. The fill material 80 need only position the embryo 42 within the cavity 34 in any manner to place the embryo 42 into functional contact with the nutritive media 26. Further, in some embodiments of the invention, the fill material 80 need only fill, either completely or partially, one or two sides of the space between the embryo 42 and the walls of the cavity 34.

Preferably, the fill material 80 is an adsorbent, such as activated charcoal, Dowex resins, zeolites, alumina, clay, diatomaceous earth, silica gel, and Kieselguhr. During assembly of the manufactured seed 20, the fill material 80 is deposited into the cavity 34 of the cylcap 22 in any manner known in the art, including manually. The fill material 80 is preferably, but not necessarily, deposited within the cavity 34 such that it substantially centers the embryo 42 within the cavity 34. Centering the embryo 42 within the cavity 34 increases the surface area of the embryo 42 in functional contact with the nutritive media 26. As used herein, the term "functional contact" is intended to mean in a position where the embryo 42 uptakes nutrients from the nutritive media 26.

In some embodiments, the fill material 80 is charcoal. Preferably, the charcoal is in the form of a powder and is activated by pretreatment with an acid such as HCl, or phosphoric acid. Activated charcoal is commercially available. For example, powdered activated carbon NORIT® CNSP or DARCO® KB-G are produced by chemical activation using a phosphoric acid process and are available from Norit Americas Inc., Marshall, Tex., 75671.

In some embodiments, the fill material 80 is nutrient-treated charcoal. As used herein, the term "nutrient-treated" charcoal refers to charcoal that has been in contact with media that contains a variety of nutrients, such as a carbon source, vitamins, minerals, and amino acids, so that the charcoal absorbs and retains nutrients from the media. A representative media used to prepare nutrient-treated charcoal is media KE64, as described in Example 1. An exemplary method for preparing nutrient-treated charcoal for use as a fill material 80 for insertion into the cavity 34 is provided in Example 1.

In accordance with the manufactured seeds and methods of the invention, nutritive media 26 (otherwise referred to as "gametophyte medium") is in functional contact with the plant embryo disposed within the manufactured seed 20. As used herein, a "nutritive medium" refers to a source of nutrients, such as vitamins, minerals, carbon, and energy sources, and other beneficial compounds used by the embryo during germination. Thus, the nutritive medium is analogous to the gametophyte of a natural seed.

In accordance with one aspect of the invention, a method is provided for producing an improved nutritive medium comprising an adsorbent material for culturing plant cells. The method in accordance with this aspect of the invention comprises (a) determining whether there is a decrease in the concentration of one or more components in a first nutritive media after incubation with a desired amount of adsorbent material; and (b) producing an improved nutritive medium comprising the same components as the first nutritive medium, wherein the improved nutritive medium comprises: (i) an increased concentration of the one or more components that was determined in step (a) to decrease in concentration in the presence of the absorbent material; and (ii) the same type of absorbent material at a concentration range within two-fold of that which was used in accordance with step (a).

In accordance with another aspect of the invention, a method is provided for producing an improved nutritive medium comprising an adsorbent material for culturing plant cells. The method in accordance with this aspect of the invention comprises: (a) incubating a first nutritive media comprising a pre-determined initial concentration of components comprising one or more carbon sources, vitamins, minerals and amino acids with a desired amount of adsorbent material to be added to an improved nutritive media; (b) determining whether there is a decrease in the concentration of one or more of the components in the first nutritive media after the incubation according to step (a) as compared to the pre-determined initial concentration of the component; and (c) producing an improved nutritive medium comprising the same components as the first nutritive medium, wherein the improved nutritive medium comprises: (i) an increased concentration of the one or more components that was determined in step (b) to decrease in concentration in the presence of the absorbent material; and (ii) the same type of absorbent material at a concentration range within two-fold of that which was used in accordance with step (a).

The methods of the present invention are useful to prepare improved nutritive medium comprising an absorbent material, such as charcoal, for use in the growth and/or germination of plant embryos. The improved nutritive medium generated according to the invention is useful for manufacturing and germinating manufactured seeds in a variety of different contexts.

In accordance with the various aspects of the invention, a first nutritive media comprising a pre-determined initial concentration of components comprising one or more carbon sources, vitamins, minerals and amino acids is incubated with an adsorbent material for a time period sufficient for the various components of the media to adbsorb to the adsorbent material. Suitable time periods for incubation of the first nutritive media with the adsorbent composition range from at least about 10 minutes up to several days or a week or longer, such as at least 15 minutes, at least 30 minutes, at least 1 hour, at least 2 hours, at least 3 hours, at least 4 hours, at least 8 hours, up to 24 hours, 48 hours, or longer.

Suitable adsorbent materials for use in the methods of making a modified (or improved) nutritive media include, but are not limited to, charcoal, polyvinyl polypyrolidone, and silica gels. In some embodiments, the adsorbent material in the first and modified (improved) nutrient media is from 1.0 g/L to 100 g/L charcoal. In some embodiments, the charcoal added to the first and modified (improved) nutritive media is from 1.0 g/L to 100 g/L of non-nutrient-treated charcoal (such as, for example, from 5 g/L, 20 g/L to 100 g/L, from 50 g/L to 100 g/L, from 60 g/L to 100 g/L, or from 50 g/L to 80 g/L, or about 60 g/L). As used herein, the term "non-nutrient-treated" charcoal refers to charcoal (e.g., plain charcoal, or activated charcoal) that has not been in contact with media that contains a variety of nutrients, such as a carbon source, vitamins, minerals, and amino acids, so that the charcoal absorbs and retains nutrients from the media.

In accordance with this aspect of the invention, the first and modified (improved) nutritive media include the same type of adsorbent composition (e.g., charcoal). The concentration of adsorbent composition in the improved nutritive media is typically within a concentration range that is about two-fold to five-fold of that of the concentration of the adsorbent that was incubated in the first nutritive medium. In some embodiments of the method, the concentration of the adsorbent composition in the improved nutritive media is the same as the concentration of the adsorbent that was incubated in the first nutritive medium.

After the first nutritive medium has been incubated with the adsorbent composition in accordance with step (a), an analysis is carried out to determine whether there is a decrease in the concentration of one or more of the components in the first nutritive medium after incubation as compared to the initial concentration of the component in the first nutritive medium. For example, TABLES 3 and 4 show a comparison of the media components before and after incubation with charcoal. For the one or more components of the nutritive medium determined to have decreased in the first nutritive medium after incubation with the adsorbent material, an adjustment is made to increase the concentration of the one or more components in the improved nutritive medium. In some embodiments of the method, an adjustment is made such that the increase in concentration of the component in the improved nutritive medium corresponds to the decrease in concentration observed in the first nutritive medium after incubation with the adsorbent composition. In some embodiments of the method, the adjustment is made to the concentration of the component in the improved nutritive medium that further takes into account at least one of (1) the effect the increased concentration of the particular component on the overall pH of the medium; (2) the interaction with other components in the medium (i.e., precipitation); or (3) a maximum level of a particular component with regard to viability of the plant embryo to be contacted with the nutritive medium.

In some embodiments, the method according to this aspect of the invention is carried out in preparation for scale-up, such that the first nutritive medium incubated with the adsorbent composition according to step (a) has a volume that is about ¼ to ¹⁄₁₀₀ (such as ⅕, ¹⁄₁₀, ¹⁄₅₀, ¹⁄₇₅ up to ¹⁄₁₀₀) of the total volume of the improved nutritive medium according to step (c).

In some embodiments, the method further comprises disposing the first nutritive medium of step (a) into a first set of manufactured seeds and disposing the improved nutritive medium of step (c) into a second set of manufactured seeds, placing a conifer embryo into functional contact with the nutritive media in each of the manufactured seeds from the first and second set of manufactured seeds, placing the manufactured seeds into an environment conducive for plant growth and comparing the germination frequencies of the embryos from the first and second set of manufactured seeds to determine if there is an effect of the improved nutritive media on the germination frequency.

In accordance with this aspect of the invention, the first nutritive medium and the modified (improved) nutritive medium typically include the same components, wherein the modified (improved) nutritive medium comprises an increased concentration of at least one or more of the components as compared to the first nutritive medium. In some embodiments of the method, the first and modified nutritive media comprise at least two components selected from the group consisting of $NH_4NO_3$, $KH_2PO_4$, Myo-inositol, Thiamine-HCL, Pyridoxine-HCL, Nicotinic Acid, Riboflavin, Ca-pantothenate, Biotin and Folic Acid, DL-serine, L-proline, L-arginine-HCL and L-alanine.

The nutritive media also typically includes $CuCl_2$, $CaCl_2$, $MgSO_4$, ferric citrate, $MnCl_2$, $H_3BO_3$, $ZnSO_4$, and $(NH_4)_2MoO_4$, as described with reference to the media designated "MS09," as described in Examples 1, 3 and 4 herein. In some embodiments, the improved nutritive media includes $FeSO_4$ at a concentration from about 5 mg/L to 25 mg/L, such as from about 10 mg/L to about 15 mg/L. In some embodiments, the improved nutritive media includes $MgSO_4$ at a concentration from about 600 mg/L to about 1500 mg/L, such as from about 800 mg/L to about 1200 mg/L.

The nutritive media may also comprise amino acids. Suitable amino acids may include amino acids commonly found incorporated into proteins as well as amino acids not commonly found incorporated into proteins, such as argininosuccinate, citrulline, canavanine, ornithine, and D-stereoisomers. In one embodiment, the nutritive medium also includes at least one amino acid selected from the group consisting of from 85 mg/L to 100 mg/L of DL-serine; from 55 mg/L to 70 mg/L of L-proline, from 300 mg/L to 600 mg/L of L-arginine-HCL, and from 55 mg/L to 70 mg/L of L-alanine.

The nutritive media typically further comprises one or more carbon sources, vitamins, and minerals. Suitable carbon sources include, but are not limited to, monosaccharides, disaccharides, and/or starches. The modified nutritive medium may also include one or more compounds involved in nitrogen metabolism, such as urea or polyamines.

The nutritive media may include oxygen-carrying substances to enhance both the absorption of oxygen and the retention of oxygen by the nutritive medium, thereby allowing the medium to maintain a concentration of oxygen that is higher than would otherwise be present in the medium solely from the absorption of oxygen from the atmosphere. Exemplary oxygen-carrying substances include perfluorocarbons, such as FC-77 and surfactants such as Pluronic F-68, available from BASF Corp., Parsippany, N.J. Exemplary oxygen-carrying substances are described in U.S. Pat. No. 5,564,224 (e.g., Col. 9, line 44, to Col. 11, line 67), herein incorporated by reference.

The nutritive media may also contain hormones. Suitable hormones include, but are not limited to, abscisic acid, cytokinins, auxins, and gibberellins. Abscisic acid is a sesquiterpenoid plant hormone that is implicated in a variety of plant physiological processes (see, e.g., Milborrow, *J. Exp. Botany* 52:1145-1164 (2001); Leung & Giraudat, *Ann. Rev. Plant Physiol. Plant Mol. Biol.* 49:199-123 (1998)). Auxins are plant growth hormones that promote cell division and growth. Exemplary auxins for use in the germination medium include, but are not limited to, 2,4-dichlorophenoxyacetic acid, indole-3-acetic acid, indole-3-butyric acid, naphthalene acetic acid, and chlorogenic acid. Cytokinins are plant growth hormones that affect the organization of dividing cells. Exemplary cytokinins for use in the germination medium include, but are not limited to, e.g., 6-benzylaminopurine, 6-furfurylaminopurine, dihydrozeatin, zeatin, kinetin, and zeatin riboside. Gibberellins are a class of diterpenoid plant hormones (see, e.g., Krishnamoorthy, *Gibberellins and Plant Growth*, John Wiley & Sons (1975)). Representative examples of gibberellins useful in the practice of the present invention include gibberellic acid, gibberellin 3, gibberellin 4, and gibberellin 7. An example of a useful mixture of gibberellins is a mixture of gibberellin 4 and gibberellin 7 (referred to as gibberellin 4/7), such as the gibberellin 4/7 sold by Abbott Laboratories, Chicago, Ill. When abscisic acid is present in the modified nutritive medium, it is typically used at a concentration in the range of from about 1 mg/L to about 200 mg/L. When present in the nutritive medium, the concentration of gibberellin(s) is typically between about 0.1 mg/L and about 500 mg/L. Auxins may be used, for example, at a concentration of from 0.1 mg/L to 200 mg/L. Cytokinins may be used, for example, at a concentration of from 0.1 mg/L to 100 mg/L.

The nutritive media may also include antimicrobials. Suitable antimicrobials are available from Sigma-Aldrich, St. Louis, Mo., sold as Product #A5955. Antimicrobials may be used, for example, at a concentration of 1 ml/L.

The methods of the invention also may be carried out with nutritive media that include a substance that causes the medium to be a semisolid or have a congealed consistency under normal environmental condition. For example, the nutritive medium may be in the form of a hydrated gel. A "gel" is a substance that is prepared as a colloidal solution and that will, or can be caused to, form a semisolid material. Such conversion of a liquid gel solution into a semisolid material is termed herein "curing" or "setting" of the gel. A "hydrated gel" refers to a water-containing gel. Such gels are prepared by first dissolving in water (where water serves as the solvent, or "continuous phase") a hydrophilic polymeric substance (serving as the solute, or "disperse phase") that, upon curing, combines with the continuous phase to form the semisolid material. Thus, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the characteristic of compliant solids, like a mass of gelatin, where the compliance becomes progressively less and the gel becomes more "solid" to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting other process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of toxicity.

Gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Examples include gelatin, agar, and agarose. Such gel solutes are termed "reversible" because reheating cured gel will re-form the gel solution. Solutions of other gel solutes require a "complexing" agent which serves to chemically cure the gel by crosslinking gel solute molecules. For example, sodium alginate is cured by adding calcium nitrate $(Ca(NO_3)_2)$ or salts of other divalent ions such as, but not limited to, calcium, barium, lead, copper, strontium, cadmium, zinc, nickel, cobalt, magnesium, and iron to the gel solution. Many of the gel solutes requiring complexing agents become irreversibly cured, where reheating will not re-establish the gel solution.

The concentration of gel solute required to prepare a satisfactory gel according to the present invention varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. In general, gels cured by complexing require less gel solute to form a satisfactory gel than "reversible" gels.

Through the practice of the methods of this aspect of the invention, the present inventors have generated a modified (improved) nutritive medium for use in manufactured seeds, as described in Example 2. As described in Examples 3 and 4, the present inventors have further discovered, through experimentation, that a manufactured seed comprising a modified nutritive media comprising from 10 g/L to 100 g/L of a non-nutrient-treated adsorbent material, and from 350 mg/L to 450 mg/L of $NH_4NO_3$, from 2000 mg/L to 3000 mg/L of $KH_2PO_4$; and at least one component selected from the group consisting of: from 150 mg/L to 300 mg/L of Myo-inositol, from 1.5 mg/L to 3.0 mg/L of Thiamine-HCl, from 0.30 mg/L to 0.80 mg/L of Pyridoxine-HCl, from 1.5 mg/L to 3.0 mg/L of Nicotinic acid, from 0.15 mg/L to 0.30 mg/L of Riboflavin, from 0.75 mg/L to 2.0 mg/L of Ca-pantothenate, from 0.01 mg/L to 0.03 mg/L of Biotin and from 0.15 mg/L to 0.30 mg/L of Folic Acid, provides an improvement in germination rate and normalcy of germinants in comparison to a manufactured seed comprising a conventional nutritive media (i.e., KE64) including 60 g/L of nutrient-treated charcoal.

In some embodiments, the modified nutritive media for use in the manufactured seed comprises about 60 g/L of non-nutrient-treated charcoal, from about 350 mg/L to about 375 mg/L of $NH_4NO_3$, from about 2000 mg/L to about 2100 mg/L of $KH_2PO_4$, and at least one component selected from the group consisting of: about 200 mg/L of Myo-inositol, about 2.0 mg/L of Thiamine-HCl, about 0.50 mg/L of Pyridoxine-HCl, about 2.0 mg/L of Nicotinic acid, about 0.26 mg/L of Riboflavin, about 1.0 mg/L of Ca-pantothenate, about 0.02 mg/L of Biotin and about 0.25 mg/L of Folic Acid.

In some embodiments, the manufactured seed further comprises a shoot restraint, wherein the shoot restraint comprises a cavity sized to receive the conifer embryo. In some embodiments, the manufactured seed further comprises a conifer embryo disposed within the cavity of the shoot restraint.

In some embodiments, the manufactured seed further comprises an adsorbent material, such as charcoal, in the cavity. In some embodiments, the charcoal in the cavity is nutrient-treated.

In one exemplary embodiment, the manufactured seed comprises a nutritive medium comprising about 60 g/L of non-nutrient-treated charcoal, from about 350 mg/L to about 375 mg/L of $NH_4NO_3$, from about 2000 mg/L to about 2100 mg/L of $KH_2PO_4$, and at least one component selected from the group consisting of: about 200 mg/L of Myo-inositol, about 2.0 mg/L of Thiamine-HCl, about 0.50 mg/L of Pyridoxine-HCl, about 2.0 mg/L of Nicotinic acid, about 0.26 mg/L of Riboflavin, about 1.0 mg/L of Ca-pantothenate, about 0.02 mg/L of Biotin and about 0.25 mg/L of Folic Acid. Media MS09, as described in Examples 1, 3 and 4 is an exemplary modified nutritive medium for use in the manufactured seeds and methods of germination as described herein.

The modified (improved) nutritive medium generated using the methods of the invention and manufactured seeds comprising the modified nutritive medium may be used for germinating a conifer embryo. The method according to this aspect of the invention comprises (a) placing a conifer embryo into functional contact with a nutritive media in a manufactured seed, the nutritive media comprising: from 10 g/L to 100 g/L of charcoal, from 350 mg/L to 450 mg/L of $NH_4NO_3$, from 2000 mg/L to 3000 mg/L of $KH_2PO_4$; and at least one component selected from the group consisting of: from 150 mg/L to 300 mg/L of Myo-inositol, from 1.5 mg/L to 3.0 mg/L of Thiamine-HCl, from 0.30 mg/L to 0.80 mg/L of Pyridoxine-HCl, from 1.5 mg/L to 3.0 mg/L of Nicotinic acid, from 0.15 mg/L to 0.30 mg/L of Riboflavin, from 0.75 mg/L to 2.0 mg/L of Ca-pantothenate, from 0.01 mg/L to 0.03 mg/L of Biotin and from 0.15 mg/L to 0.30 mg/L of Folic Acid; and (b) placing the manufactured seed in an environment conducive for plant growth so as to allow the embryo to grow and germinate from the manufactured seed.

As described supra, the present inventors have discovered, through experimentation, that a manufactured seed comprising a modified nutritive media improves the germination frequency of conifer embryos in comparison to a standard nutritive media (e.g., KE64). The modified nutritive media described herein in connection with the manufactured seeds is also useful in the methods for germinating an embryo. In some embodiments of the method, the charcoal in the modified nutritive media is non-nutrient treated prior to addition to the media. In some embodiments, the modified nutritive media comprises from 10 g/L to 100 g/L charcoal. In some embodiments, the charcoal added to the modified nutritive media is from 10 g/L to 100 g/L of non-nutrient-treated charcoal (such as, for example, from 20 g/L to 100 g/L, from 50 g/L to 100 g/L, from 60 g/L to 100 g/L, or from 50 g/L to 80 g/L, or about 60 g/L).

In some embodiments of the method, the modified nutritive media for use in the manufactured seed comprises about 60 g/L of non-nutrient-treated charcoal, from about 350 mg/L to about 375 mg/L of $NH_4NO_3$, from about 2000 mg/L to about 2100 mg/L of $KH_2PO_4$, and at least one component selected from the group consisting of: about 200 mg/L of Myo-inositol, about 2.0 mg/L of Thiamine-HCl, about 0.50 mg/L of Pyridoxine-HCl, about 2.0 mg/L of Nicotinic acid, about 0.26 mg/L of Riboflavin, about 1.0 mg/L of Ca-pantothenate, about 0.02 mg/L of Biotin and about 0.25 mg/L of Folic Acid.

The following examples merely illustrate the best mode now contemplated for practicing the invention, but should not be construed to limit the invention.

Example 1

This Example provides a representative method of preparation of suitable nutritive medium, nutrient-treated charcoal, and representative manufactured seeds suitable for use in the methods of the invention.

Methods:

1. Nutritive Media (KE64-50):

is made by combining KE64 Basic Media (Table 1) with the components from Table 2, as described. KE64-50 is prepared from pre-made stocks. The required amount of each stock solution (that is not heat-labile) is added to water. Non-stock chemicals (such as charcoal and agar) are weighed out and added directly to the medium. After all the nonheat-labile chemicals and compounds are added, the medium is brought up to an appropriate volume and the pH is adjusted to 5.7. The medium is then sterilized by autoclaving for 25 minutes.

TABLE 1

Formulation of KE64 Basic Media

| Medium Component | Final Concentration (mg/l) |
| --- | --- |
| $NH_4NO_3$ | 301.1 |
| $H_3BO_3$ | 10.0 |
| $(NH_4)_2MoO_4$ | 0.06 |
| $CaCl_2$—$2H_2O$ | 299.2 |
| $KH_2PO_4$ | 1800.0 |
| $MgSO_4$—$7H_2O$ | 1000.0 |
| $MnCl_2$•$4H_2O$ | 6.0 |
| $ZnSO_4$—$7H_2O$ | 0.8 |
| $CuCl_2$—$2H_2O$ | 0.5 |
| Ferric Citrate | 60 mg/L |
| Pluronic F-68 | 10 g/l |
| Agar | 18 g/l |

Filter-sterilized heat-labile components (Table 2) are added after the medium has cooled to 40° C.

TABLE 2

Components added to KE64 Basic Media

| Medium Component | Final Concentration mM | Final Concentration (mg/l) |
| --- | --- | --- |
| Myo-inositol | 0.5549 | 100.0 |
| Thiamine-HCl | 0.0030 | 1.0 |
| Pyridoxine-HCl | 0.0012 | 0.25 |
| Nicotinic acid | 0.0081 | 1.0 |
| Riboflavin | 0.0021 | 0.125 |
| Ca-pantothenate | | 0.50 |

TABLE 2-continued

Components added to KE64 Basic Media

| Medium Component | Final Concentration mM | Final Concentration (mg/l) |
| --- | --- | --- |
| Biotin | 0.0003 | 0.0010 |
| Folic acid | 0.8077 | 0.1250 |
| L-asparagine | 1.8255 | 106.7 |
| L-glutamine | 0.3646 | 266.7 |
| L-lysine-2HCl | 0.7612 | 53.3 |
| DL-serine | 0.4631 | 80 |
| L-proline | 1.5310 | 53.3 |
| L-arginine-HCl | 0.4552 | 266.7 |
| Urea | 13.3200 | 800 |
| L-valine | 0.5983 | 53.3 |
| L-alanine | 0.2203 | 53.3 |
| L-leucine | 0.2448 | 80 |
| L-threonine | 0.3226 | 26.7 |
| L-phenylalanine | 0.1720 | 53.3 |
| L-histidine | 0.1308 | 26.7 |
| L-tryptophan | 0.2035 | 26.7 |
| L-isoleucine | 1.2930 | 26.7 |
| L-methionine | 0.7100 | 26.7 |
| L-glycine | 0.0003 | 53.3 |
| L-tyrosine | 0.2242 | 53.3 |
| L-cysteine | 0.6098 | 26.7 |
| Sucrose | | 50 g/l |
| Gibberillic Acid ($GA_{4/7}$) | | 0.1 |
| Antimicrobials | | 1.0 ml/l |

2. Preparation of Charcoal for Addition to the Media and/or to the Corrosion Cavity of the Manufactured Seeds A. Preparation of Nutrient-treated Charcoal:

KE64 Basic Media (Table 1) is prepared as described above without Pluronic F-68 and without agar. 23.3 grams of 100-mesh charcoal is added to 1 liter of KE64 Basic Media. The components are autoclaved, and allowed to cool to 40° C. The components of Table 2, as described in Example 1, are added sterilely to the KE64 Basic media, and the media is stirred for at least 2 hours to mix the components. The media is filtered through Whatman #1 filter paper in a Buchner funnel to collect the charcoal. A moisture balance is used to determine the moisture content of the charcoal cake, and the dry weight of the charcoal is calculated. If the nutrient-treated charcoal is to be added to the cavity of the manufactured seed, it is first dried until it becomes flowable matter.

B. Preparation of Non-Nutrient-Treated Charcoal:

100-mesh charcoal which was chemically activated using a phosphoric acid process (NORIT® CNSP) was obtained from Norit Americas Inc., Marshall, Tex.

3. Preparation of Manufactured Seeds:

Representative methods used for making manufactured seeds are described in U.S. Pat. Nos. 6,119,395; 5,701,699; and 5,427,593, incorporated herein by reference.

Generally described, manufactured seeds include a seed coat (24), nutritive medium (26), a plant embryo (42), and optionally a cotyledon restraint (22). A manufactured seed that does not include a plant embryo (42) is known in the art as a "seed blank." The seed blank typically is a cylindrical capsule having a closed end and an open end.

The nutritive media (26), also referred to as "Gametophyte Media" is analogous to the gametophyte of a natural seed, and is placed within the seed coat to substantially fill the interior of the seed coat. Exemplary nutritive media (26) for use in the manufactured seeds includes KE64 described above, or a modified nutritive media, as described herein which may include from 0 g/L to 100 g/L of an adsorbent composition such as charcoal. The charcoal for use in the nutritive media may be pre-treated with nutrients, as described above, or may be plain, non-nutrient-treated charcoal.

A longitudinally extending hard porous insert, known as a cotyledon restraint (22), is centrally located within one end of the seed coat surrounded by the nutritive media and includes a centrally located cavity (34), also referred to as a "corrosion cavity" extending partially through the length of the cotyledon restraint. The cavity (34) is sized to receive a plant embryo (42) therein. The well-known plant embryo includes a radicle end and a cotyledon end. The plant embryo is deposited within the cavity of the cotyledon restraint (22), cotyledon end first. The plant embryo is then sealed within the seed blank by an end seal (43). A weakened spot in the end seal (43) allows the radicle end of the plant embryo to penetrate the end seal.

In an exemplary method for preparing a manufactured seed for use in the invention, the seed coat is prepared by sectioning polycaprolactone tubing to the appropriate length. Ceramic shoot restraints are made by injecting a porcelain slip into a preformed mold with a pin in the center to create the shoot accepting cavity. The slip is allowed to dry to a consistency that allows removal of the preformed restraint. The restraint is subsequently heated to a temperature that allows the porcelain to form a porous, but fused structure. The restraint can be acid washed to remove impurities, if desired. Lids are made by pre-stretching Parafilm™ (Pechiney Plastic Packaging, Chicago, Ill. 60631).

Manufactured seed are assembled by thermobonding the ceramic shoot restraint (22) to the seed coat (24). The seed coat (24) is then filled with nutritive media (26) and an embryo is inserted into the cavity (34) in the cotyledon restraint (22), cotyledon end first. Dry charcoal fill material (80) (either nutrient-treated or non-nutrient-treated) may be loaded into the cotyledon restraint after the embryo is inserted into the cavity (34). After the charcoal has been added, the seeds are then sealed with a secondary end seal by laying it over the open end of the seed and fusing the lids to the surface with heat. The primary end seals are dipped into blue wax mixture prior to attaching the secondary end seal. This promotes good bonding between the primary and secondary end seals. The seeds are then swabbed with anti-microbial agents.

4. Preparation of Plant Embryos:

Zygotic embryos are prepared from botanic seeds. The seeds are surface-sterilized by methods similar to those previously described (Cyr et al., *Seed Sci. Res.* 1:91-97 (1991)). The seeds are cracked open and the zygotic embryos are dissected from the megagametophyte with scalpel and forceps in a laminar flow hood.

Somatic embryos are produced according to standard methods previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation medium that includes hormones to initiate the formation of embryogenic cells, such as embryonic suspensor masses that are capable of developing into somatic embryos. The embryogenic cells may then be further cultured in a maintenance medium that promotes establishment and multiplication of the embryogenic cells. Subsequently, the multiplied embryogenic cells may be cultured in a development medium that promotes the development of somatic embryos, which may further be subjected to post-development treatments such as cold treatments. The somatic embryos used in the methods of the invention have completed the development stage of the somatic embryogenesis process. They may also have been subjected to one or more post-development treatments.

5. Germination:

A suitable amount of sterile sand is prepared by baking 2 liters of sand at a temperature of 375° F. for 24 hours. The sand is then added to pre-sterilized trays and 285 ml water is added. Furrows are then formed and the box is sealed. The box containing the sand is then autoclaved for 1 hour at 121° C. and 1 atmosphere pressure.

The manufactured seeds are sown in the sand and allowed to germinate. Typically, the manufactured seeds are cultured under continuous light at room temperature (23° C.) for four to five weeks.

Several parameters may be measured to determine the germination frequency of the manufactured seeds and the quality of the germinants.

At a designated time after sowing, the lengths of the radicle, hypocotyl, cotyledons, and epicotyl of the germinants may be measured.

The term "radicle" refers to the part of a plant embryo that develops into the primary root of the resulting plant.

The term "cotyledon" refers generally to the first, first pair, or first whorl (depending on the plant type) of leaf-like structures on the plant embryo that function primarily to make food compounds in the seed available to the developing embryo, but in some cases act as food storage or photosynthetic structures.

The term "hypocotyl" refers to the portion of a plant embryo or seedling located below the cotyledons but above the radicle.

The term "epicotyl" refers to the portion of the seedling stem that is above the cotyledons.

The germination rate may be measured and the normalcy of the germinants may also be assessed. A "normal germinant" or "normalcy" denotes the presence of all expected parts of a plant at time of evaluation. In the case of gymnosperms, normalcy is characterized by the radicle having a length greater than 3 mm and no visibly discernable malformations compared to the appearance of embryos germinated from natural seed. "Not normal" means tissue on at least one organ is swollen, and the root and cotyledons are dead. "Not-normal fully extracted" means the germinant has fully emerged from the cavity but is not normal. "Unchanged" means embryo has not changed from day one of the experiment (i.e., no germination has occurred).

Example 2

This Example describes the preparation of a modified nutritive medium for use in manufactured seeds containing non-nutrient-treated charcoal.

Methods:

The KE64 medium, made as described in Example 1, was incubated in the presence or absence of nutrient-treated or non-nutrient-treated charcoal, and the concentration of the media components were measured after incubation.

The nutrient-treated 100 mesh charcoal was prepared as described in Example 1.

Conditions Tested:

1. KE64 Media with no charcoal added (sample 012).
2. KE64 Media plus 60 g/L 100 mesh non-nutrient-treated charcoal (sample 013).
3. KE64 Media plus 60 g/L 100 mesh nutrient-treated charcoal (sample 014).

The charcoal was added where indicated, mixed, and incubated for 2 hours. The concentration of the media components were analyzed as shown below in Table 3.

TABLE 3

Comparison of Measured Concentration of Media Components
before and after incubation in the presence of charcoal.
The measurements are in mg/L unless otherwise indicated.

| Medium Component | KE64 Medium (no charcoal) Final Concentration Expected (mg/L) "B" | KE64 Media (no charcoal) Measured concentration (mg/L) "C" | KE64 Media plus charcoal (non-treated) Measured concentration (mg/L) "D" | KE64 Media plus charcoal (nutrient treated) Measured concentration (mg/L) "E" |
|---|---|---|---|---|
| $NH_4NO_3$ | 301.1 | 322.3 | 296.8 | 381.3 |
| $H_3BO_3$ | 10.0 | 11.4 | 9.7 | 11.4 |
| $(NH_4)_2MoO_4$ | 0.06 | 0.08 | 0.02 | 0.02 |
| $CaCl_2$—$2H_2O$ | 299.2 | 275.9 | 124.7 | 271.1 |
| $KH_2PO_4$ | 1800.0 | 1573 | 2513 | 1907 |
| $MgSO_4$—$7H_2O$ | 1000.0 | 987.3 | 635.6 | 960.9 |
| $MnCl_2 \cdot 4H_2O$ | 6.0 | 3.8 | 1.7 | 3.9 |
| $ZnSO_4$—$7H_2O$ | 0.8 | 0.15 | 0.09 | 0.10 |
| $CuCl_2$—$2H_2O$ | 0.5 | 0.27 | <0.01 | <0.01 |
| Myo-inositol | 100.0 | ND | ND | ND |
| Thiamine-HCl | 1.0 | ND | ND | ND |
| Pyridoxine-HCl | 0.25 | ND | ND | ND |
| Nicotinic acid | 1.0 | ND | ND | ND |
| Riboflavin | 0.13 | ND | ND | ND |
| Ca-pantothenate | 0.50 | ND | ND | ND |
| Biotin | 0.0010 | ND | ND | ND |
| Folic Acid | 0.1250 | ND | ND | ND |
| L-asparagine/Serine | 187 | 191 | 155 | 204 |
| L-Glutamine/Histidine | 293 | 231 | 166 | 206 |
| L-Lysine-HCl | 53.3 | 43 | 21 | 32 |
| DL-Serine | 80.0 | ND | ND | ND |
| L-Proline | 53.3 | 94 | 87 | 100 |
| L-Arginine-HCl | 266.7 | 256 | 43 | 76 |
| L-Valine | 53.3 | 50 | 41 | 49 |
| L-Alanine | 53.3 | 45 | 40 | 49 |
| L-Leucine | 80.0 | 75 | 48 | 64 |
| L-Threonine | 26.7 | 44 | 37 | 42 |
| L-Phenylalanine | 53.3 | 51 | 5 | 10 |
| L-Tryptophan | 26.7 | 19 | ND | ND |
| L-Isoleucine | 26.7 | 25 | 16 | 22 |
| L-Methionine | 26.7 | 18 | ND | ND |
| L-Glycine | 53.3 | 52 | 40 | 51 |
| L-Tyrosine | 53.3 | 56 | 3 | 6 |
| L-Cysteine | 26.7 | ND | ND | ND |
| Sucrose | 50.0 g/L | 52.8 g/L | 49.2 g/L | 63.2 g/L |
| Urea | 800 | ND | ND | ND |

TABLE 4

Analysis of Results of TABLE 3

| Medium Component | concentration absorbed to charcoal mg/L (C − D) "F" | Gain in nutrient concentration of supernatant due to adding treated charcoal to media mg/L (E − C) "G" | Media Adjustment factor E/C "H" | New Starting concentration (H × B) "I" |
|---|---|---|---|---|
| $NH_4NO_3$ | 25.5 | 59.0 | 1.2 | 361.3 |
| $H_3BO_3$ | 1.7 | 0.0 | 1.0 | 10.00 |
| $(NH_4)_2MoO_4$ | 0.1 | −0.1 | 1.0 | 0.1 |
| $CaCl_2$—$2H_2O$ | 151.1 | −4.8 | 1.0 | 299.2 |
| $KH_2PO_4$ | −940.3 | 333.9 | 1.1 | 2059.8 |
| $MgSO_4$—$7H_2O$ | 351.7 | −26.4 | 1.0 | 1000.0 |
| $MnCl_2 \cdot 4H_2O$ | 2.1 | 0.1 | 1.0 | 6.0 |
| $ZnSO_4$—$7H_2O$ | 0.10 | −0.1 | 1.0 | 0.8 |
| $CuCl_2$—$2H_2O$ | ND | ND | 1.0 | 0.5 |
| Myo-inositol | ND | ND | ND | 100.0 |
| Thiamine-HCl | ND | ND | ND | 1.0 |
| Pyridoxine-HCl | ND | ND | ND | 0.3 |
| Nicotinic acid | ND | ND | ND | 1.0 |
| Riboflavin | ND | ND | ND | 0.1 |
| Ca-pantothenate | ND | ND | ND | 0.5 |
| Biotin | ND | ND | ND | 0.0 |
| Folic Acid | ND | ND | ND | 0.1 |

TABLE 4-continued

Analysis of Results of TABLE 3

| Medium Component | concentration absorbed to charcoal mg/L (C − D) "F" | Gain in nutrient concentration of supernatant due to adding treated charcoal to media mg/L (E − C) "G" | Media Adjustment factor E/C "H" | New Starting concentration (H × B) "I" |
|---|---|---|---|---|
| L-asparagine/Serine | 36.0 | 13.0 | 1.1 | L-Asparagine: 117.4 Serine: 88.0 |
| L-Glutamine/Histidine | 65.0 | −25.0 | 1.0 | L-Glutamine: 266.7 L-Histidine: 26.7 |
| L-Lysine-HCl | 22.0 | −25.0 | 1.0 | 53.3 |
| L-Proline | 7.0 | 6.0 | 1.1 | 58.6 |
| L-Arginine-HCl | 213.0 | −180.0 | 2.0 | 533.4 |
| L-Valine | 9.0 | −1.0 | 1.0 | 53.3 |
| L-Alanine | 5.0 | 4.0 | 1.1 | 58.6 |
| L-Leucine | 27.0 | −11.0 | 1.0 | 80.0 |
| L-Threonine | 7.0 | −2.0 | 1.0 | 26.7 |
| L-Phenylalanine | 46.0 | −41.0 | 1.0 | 53.3 |
| L-Isoleucine | 9.0 | −3.0 | 1.0 | 26.7 |
| L-Glycine | 12.0 | −1.0 | 1.0 | 53.3 |
| L-Tyrosine | 53.0 | −50.0 | 1.0 | 53.3 |
| L-Cysteine | ND | ND | ND | 53.3 |
| Sucrose | 3.6 | 10.4 | 1.2 | 60.0 |
| Urea | ND | ND | 1.0 | 800.0 |

TABLE 5

Modified Nutritive Media MS08 and MS09

| Medium Component | KE64 Medium Final Concentration (mg/L) | MS08 Final Concentration (mg/L) | MS09 Final Concentration (mg/L) |
|---|---|---|---|
| $NH_4NO_3$ | 301.1 | 301.1 | 371.7 |
| $H_3BO_3$ | 10.0 | 10.0 | 10.0 |
| $(NH_4)_2MoO_4$ | 0.06 | 0.06 | 0.06 |
| $CaCl_2$—$2H_2O$ | 299.2 | 299.2 | 299.2 |
| $KH_2PO_4$ | 1800.0 | 2088 | 2088 |
| $MgSO_4$—$7H_2O$ | 1000.0 | 1000 | 1000 |
| $MnCl_2 \cdot 4H_2O$ | 6.0 | 6.0 | 6.0 |
| $ZnSO_4$—$7H_2O$ | 0.8 | 0.8 | 0.8 |
| $CuCl_2$—$2H_2O$ | 0.5 | 0.5 | 0.5 |
| Ferric Citrate | 60 mg/l | 60 | 60 |
| Myo-inositol | 100 | 100 | 200 |
| Thiamine-HCl | 1.0 | 1.0 | 2.0 |
| Pyridoxine-HCl | 0.25 | 0.25 | 0.50 |
| Nicotinic acid | 1.0 | 1.0 | 2.0 |
| Riboflavin | 0.125 | 0.13 | 0.26 |
| Ca-pantothenate | 0.50 | 0.50 | 1.0 |
| Biotin | 0.0010 | 0.01 | 0.02 |
| Folic Acid | 0.1250 | 0.13 | 0.25 |
| L-asparagine | 106.7 | 11.73 | 11.73 |
| L-glutamine | 266.7 | 266.7 | 266.7 |
| L-lysine-2HCl | 53.3 | 53.3 | 53.3 |
| DL-serine | 80.0 | 88.0 | 88.0 |
| L-proline | 53.3 | 58.63 | 58.63 |
| L-arginine-HCl | 266.7 | 533.3 | 533.3 |
| Urea | 800.0 | 800 | 800 |
| L-valine | 53.3 | 53.3 | 53.3 |
| L-alanine | 53.3 | 58.63 | 58.63 |
| L-leucine | 80.0 | 80.0 | 80.0 |
| L-threonine | 26.7 | 26.7 | 26.7 |
| L-phenylalanine | 53.3 | 53.3 | 53.3 |
| L-histidine | 26.7 | 26.7 | 26.7 |
| L-tryptophan | 26.7 | 26.7 | 26.7 |
| L-isoleucine | 26.7 | 26.7 | 26.7 |
| L-methionine | 26.7 | 26.7 | 26.7 |
| L-glycine | 53.3 | 53.3 | 53.3 |
| L-tyrosine | 53.3 | 53.3 | 53.3 |
| L-cysteine | 26.7 | 26.7 | 26.7 |
| Pluronic F-68 | 10 g/l | 9.0 g/l | 9.0 g/l |
| Charcoal | 60 g/l (nutrient-treated) | 60.0 g/l (non-nutrient-treated) | 60.0 g/l (non-nutrient-treated) |
| Agar | 18 g-26 g/l | 18.0 g/l | 18.0 g/l |
| pH | | 5.7 | 5.7 |
| Sucrose | 50 g/l | 60.0 g/l | 60.0 g/l |

TABLE 6

Summary of components that differ in modified media MS-08 and MS-09 in comparison to KE64

| Medium Component | KE64 Medium Final Concentration (mg/L) | MS08 Final Concentration (mg/L) | MS09 Final Concentration (mg/L) |
|---|---|---|---|
| $NH_4NO_3$ | 301.1 | 301.1 | 371.7 |
| $KH_2PO_4$ | 1800.0 | 2088 | 2088 |
| Myo-inositol | 100 | 100 | 200 |
| Thiamine-HCl | 1.0 | 1.0 | 2.0 |
| Pyridoxine-HCl | 0.25 | 0.25 | 0.50 |
| Nicotinic acid | 1.0 | 1.0 | 2.0 |
| Riboflavin | 0.125 | 0.13 | 0.26 |
| Ca-pantothenate | 0.50 | 0.50 | 1.0 |
| Biotin | 0.0010 | 0.01 | 0.02 |
| Folic Acid | 0.1250 | 0.13 | 0.25 |
| L-asparagine | 106.7 | 11.73 | 11.73 |
| DL-serine | 80.0 | 88.0 | 88.0 |
| L-proline | 53.3 | 58.63 | 58.63 |
| L-arginine-HCl | 266.7 | 533.3 | 533.3 |
| L-alanine | 53.3 | 58.63 | 58.63 |
| Charcoal | 60 g/l (nutrient-treated) | 60.0 g/l (non-nutrient-treated) | 60.0 g/l (non-nutrient-treated) |

TABLE 6-continued

Summary of components that differ in modified media MS-08 and MS-09 in comparison to KE64

| Medium Component | KE64 Medium Final Concentration (mg/L) | MS08 Final Concentration (mg/L) | MS09 Final Concentration (mg/L) |
|---|---|---|---|
| Agar | 18 g-26 g/l | 18.0 g/l | 18.0 g/l |
| pH | | 5.7 | 5.7 |
| Sucrose | 50 g/l | 60.0 g/l | 60.0 g/l |

It is noted that concentration of some of the components, such as L-Tyrosine, L-Phenylalanine, and Ferric Citrate were adjusted to account for pH and to avoid precipitation problems.

Example 3

This Example describes a comparison of the effect of various nutritive media formulations KE64, MS08 and MS09 used in manufactured seed on germination frequency and quality in Loblolly Pine.

Methods:

Zygotic Loblolly pine seeds were surface sterilized, embryos were removed and inserted in the manufactured seed, as described in Example 1.

Manufactured seeds were prepared as described in Examples 1 and 2, with the use of ceramic cotyledon restraints, with the variations in nutritive media and either nutrient treated or non-nutrient-treated charcoal included in the cavity as indicated below. Nutritive media KE64 was made as described in Example 1. Nutrient-treated charcoal was prepared as described in Example 1. MS08 and MS09 media were made as described in Example 2.

Once the manufactured seed blanks were assembled, for the indicated constructs, 100 mesh, dry, nutrient-treated charcoal or non-nutrient-treated charcoal was then pipetted into the corrosion cavity of the construct using a sterile Pasteur Pipette. The embryos were then inserted into the cotyledon restraint.

The nutritive media was prepared as shown below and was placed within the seed coat to substantially fill the interior of the seed coat. In some treatment conditions the nutritive media contained charcoal that was nutrient-treated, and in other treatment conditions, the media contained charcoal that was not nutrient treated.

As described above in Example 2, MS08 and MS09 were formulated to increase the concentration of certain media components, shown in Tables 5 and 6, in comparison to KE64 to attempt to enhance, or at least maintain the same germination frequency observed with KE64 in the presence of nutrient-treated charcoal.

The media dispensing temperature was 45° C. The live end of the manufactured seed (end with the embryo cavity) were dipped in wax.

108 seeds were tested per treatment (4 treatments), resulting in a total of 432 seeds.

Treatment Conditions Tested:

1. KE64 Complete Media (50 g/l sucrose; 18 g/L agar), plus 60 g/L nutrient-treated charcoal in media and nutrient-treated charcoal in the cavity.

2. MS08 Complete Media (60 g/L sucrose; 18 g/L agar), plus 60 g/L non-nutrient-treated charcoal in media and nutrient-treated charcoal in the cavity.

3. MS09 Complete Media (60 g/L sucrose; 18 g/L agar), plus 60 g/L non-nutrient-treated charcoal in media and nutrient-treated charcoal in the cavity.

4. KE64 Complete Media (50 g/L sucrose; 18 g/L agar), plus 60 g/L non-nutrient treated charcoal in media and nutrient-treated charcoal in the cavity.

Manufactured seeds assembled as described above for each treatment condition were sown in boxes of sterile sand and placed in a light room. The seeds were scored for germination at 25 days past sowing.

Results:

The results are shown below in Tables 7 and 8.

TABLE 7

Organ Lengths and % Laterals

| Media | Laterals (%) | Radical Length (mm) | Hypocotyl Length (mm) | Cotyledon Length (mm) | Epicotyl Length (mm) |
|---|---|---|---|---|---|
| Treatment #1 (KE64 plus 60 g/L nutrient-treated charcoal in media) | 25.3% | 27.0 | 22.7 | 19.5 | 8.2 |
| Treatment #2 (MS08 plus 60 g/L non-nutrient-treated charcoal in media) | 20.4% | 27.0 | 23.3 | 21.2 | 10.6 |
| Treatment #3 (MS09 plus 60 g/L non-nutrient-treated charcoal in media) | 43.0% | 28.9 | 28.1 | 20.5 | 9.5 |
| Treatment #4 (KE64 plus 60 g/L non-nutrient-treated charcoal in media) | 4.3% | 10.9 | 14.6 | 16.4 | 4.7 |

TABLE 8

Quality of Germinants

| Media | Normal Germinants (%) | Would be normal if fully extracted (%) | Total normal germinants: (col 1 + col 2) | Abnormal Germinants (%) | Unchanged (%) |
|---|---|---|---|---|---|
| Treatment #1 (KE64 plus 60 g/L nutrient-treated charcoal in media) | 30.3% | 5.1% | 35.4% | 38.4% | 26.3% |
| Treatment #2 (MS08 plus 60 g/L non-nutrient-treated charcoal in media) | 22.1% | 2.1% | 24.2% | 32.6% | 43.2% |

TABLE 8-continued

Quality of Germinants

| Media | Normal Germinants (%) | Would be normal if fully extracted (%) | Total normal germinants: (col 1 + col 2) | Abnormal Germinants (%) | Unchanged (%) |
|---|---|---|---|---|---|
| Treatment #3 (MS09 plus 60 g/L non-nutrient-treated charcoal in media) | 44.7% | 10.6% | 55.3% | 26.6% | 18.1% |
| Treatment #4 (KE64 plus 60 g/L non-nutrient-treated charcoal in media) | 3.2% | 2.1% | 5.3% | 43.6% | 51.1% |

Discussion of Results:

As shown above in Table 8, the manufactured seeds with MS09 with 60 g/L non-nutrient-treated charcoal in the media performed better than KE64 with 60 g/L nutrient-treated charcoal in the media, wherein the KE64 containing seeds resulting in a 44.7% germination frequency of normal germinants, and an overall frequency of normal plus normal, but not fully extracted germinants of 55.3% in comparison to the MS09 containing seeds which generated 30.3% normal germination frequency, and an overall germination frequency of 35.4% normal plus normal but not fully extracted germinants.

The MS08 media with 60 g/L non-nutrient-treated media did not perform as well as either KE64 or MS09.

As further shown in Table 7, the manufactured seeds with MS09 media (with non-nutrient-treated charcoal in the media) produced germinants having organ sizes at least as large, if not larger, than the germinants produced from the standard KE64 media (with nutrient-treated charcoal in the media).

Overall Conclusion:

It appears that MS09 is superior to both KE64 and MS08 for use in manufactured seeds with Loblolly pine with regard to the frequency and quality of resulting germinants. The use of this modified media (MS09) provides the advantage of avoiding the time and cost involved in the lengthy preparation of nutrient-treated charcoal for use in manufactured seeds.

It is noted that an additional experiment was carried out with Loblolly pine embryos to compare manufactured seeds containing either KE64 with 60 g/L non-nutrient-treated charcoal or MS09 with 60 g/L non-nutrient-treated charcoal, with germination results assessed at 49 days past sowing, however, this experiment did not produce statistically significant data, likely due to contamination issues.

Example 4

This Example describes the effect of various nutritive media used in manufactured seed on germination frequency and quality in Douglas fir embryos.

Methods:

Douglas-fir somatic embryos from two different genotypes (genotype #1 and #2) were cultured up to the development stage as described in Example 1. These embryos were then placed on stratification media for 4 weeks and assessed for sterility prior to insertion into manufactured seeds.

Manufactured seeds were prepared as described in Example 1, with the use of either Type A ceramic cotyledon restraints or Type B ceramic cotyledon restraints, with the variations in nutritive media and either nutrient treated or non-nutrient-treated charcoal included in the cavity as indicated below. Nutritive media KE64 was made as described in Example 1. Nutrient-treated charcoal was prepared as described in Example 1. MS09 media was made as described in Example 2.

Once the manufactured seed blanks were assembled, for the indicated constructs, 100 mesh, dry, nutrient-treated charcoal or non-nutrient-treated charcoal was then pipetted into the corrosion cavity of the construct using a sterile Pasteur Pipette. The embryos were then inserted into the cotyledon restraint.

The nutritive media was prepared as shown below and was placed within the seed coat to substantially fill the interior of the seed coat. In some treatment conditions, the nutritive media contained charcoal that was nutrient-treated, and in other treatment conditions, the media contained charcoal that was not nutrient treated.

As described above in Example 2, MS09 was formulated to increase the concentration of certain media components, shown in Tables 5 and 6, in comparison to KE64 to attempt to enhance, or at least maintain the same germination frequency observed with KE64 in the presence of nutrient-treated charcoal.

The media dispensing temperature was 45° C. The live end of the manufactured seed (end with the embryo cavity) were dipped in wax.

Each treatment in this study consisted of 7 replicates with 10 seeds/replicate treatment, for a total of 280 seeds.

The treatment conditions as described below in Table 9. The manufactured seeds containing embryos were sown into 7 sterile sand boxes with 10 seeds/treatment/box. The seeds were scored with respect to germination frequency and organ lengths at 61 days past sowing.

TABLE 9

Treatment Conditions for the Preparation of Manufactured Seeds Using genotypes #1 and #2 of Douglas-fir Somatic Embryos

| Treatment | Genotypes tested | Nutritive Media | Charcoal in Nutritive media | Charcoal in cavity | Cotyledon Restraint |
|---|---|---|---|---|---|
| 1 | #1 #2 | KE64 | nutrient-treated (60 g/L) | nutrient-treated charcoal in cavity | Type B |

TABLE 9-continued

Treatment Conditions for the Preparation of Manufactured Seeds Using genotypes #1 and #2 of Douglas-fir Somatic Embryos

| Treatment | Genotypes tested | Nutritive Media | Charcoal in Nutritive media | Charcoal in cavity | Cotyledon Restraint |
|---|---|---|---|---|---|
| 2 | #1 | MS09 | non-nutrient-treated charcoal (60 g/L) | nutrient-treated charcoal in cavity | Type B |
| 3 | #1 #2 | KE64 | nutrient-treated charcoal (60 g/L) | nutrient-treated charcoal in cavity | Type B |
| 4 | #2 | MS09 | non-nutrient-treated charcoal (60 g/L) | nutrient-treated charcoal in cavity | Type B |
| 5 | #1 | KE64 | nutrient-treated charcoal (60 g/L) | no charcoal in cavity | Type A |
| 6 | #2 | KE64 | nutrient-treated charcoal (60 g/L) | no charcoal in cavity | Type A |

TABLE 10

Organ Lengths for All Treatments (mm)

| Treatment | Radical length (mm) $\alpha = 0.0014$ | Hypocotyl length (mm) $\alpha = 0.0001$ | Cotyledon length (mm) $\alpha = 0.0001$ | Epicotyl Length (mm) $\alpha = 0.6717$ |
|---|---|---|---|---|
| #1 (geno#1/#2: KE64: treated charcoal in media and cavity) | 9.51 mm$^B$ | 10.46$^C$ | 5.34$^B$ | 0.00 |
| #2 (geno#1: MS09: non-treated charcoal in media, treated charcoal in cavity) | 12.89 mm$^{AB}$ | 13.00 mm$^C$ | 7.24 mm$^{AB}$ | 7.75 mm |
| #3 (geno#1/#2: KE64: treated charcoal in media, treated charcoal in cavity) | 6.93 mm$^B$ | 11.26 mm$^{BC}$ | 5.15 mm$^B$ | 5.40 mm |
| #4 (geno#2: MS09: non-treated charcoal in media, treated charcoal in cavity) | 7.81 mm$^B$ | 10.47 mm$^{BC}$ | 5.15 mm$^B$ | 2.60 mm |
| #5 (geno #1: KE64: treated charcoal in media, no charcoal in cavity) | 15.71 mm$^{AB}$ | 14.76 mm$^A$ | 9.57 mm$^A$ | 3.51 mm |
| #6 (geno #2: KE64: treated charcoal in media, no charcoal in cavity) | 23.04 mm$^A$ | 17.45 mm$^A$ | 9.03 mm$^A$ | 3.52 mm |

TABLE 11

Germination Frequency in Douglas-fir

| Treatment | Full Germination $\alpha = 0.0013^1$ | Partial Germination $\alpha = 0.0087$ | Total Germination (col 1 + 2) | Root in Air$^2$ $\alpha = 0.4614$ | No Germination $\alpha = 0.0011$ |
|---|---|---|---|---|---|
| #1 (geno#1/#2: KE64: treated charcoal in media and cavity) | 0.0%$^B$ | 11.1%$^{AB}$ | 11.1% | 11.1% | 75.9%$^A$ |
| #2 (geno#1: MS09: non-treated charcoal in media, treated charcoal in cavity) | 1.9%$^{AB}$ | 25.9%$^{AB}$ | 27.8% | 7.4% | 64.8%$^{AB}$ |
| #3 (geno#1/#2: KE64: treated charcoal in media, treated charcoal in cavity) | 0.0%$^B$ | 5.6%$^B$ | 5.6% | 16.7% | 77.8%$^A$ |
| #4 (geno#2: MS09: non-treated charcoal in media, treated charcoal in cavity) | 0.0%$^B$ | 18.5%$^{AB}$ | 18.5% | 14.8% | 66.7%$^{AB}$ |

TABLE 11-continued

Germination Frequency in Douglas-fir

| Treatment | Full Germination $\alpha = 0.0013^1$ | Partial Germination $\alpha = 0.0087$ | Total Germination (col 1 + 2) | Root in Air$^2$ $\alpha = 0.4614$ | No Germination $\alpha = 0.0011$ |
|---|---|---|---|---|---|
| #5 (geno #1: KE64: treated charcoal in media, no charcoal in cavity) | 11.1%$^A$ | 22.2%$^{AB}$ | 33.3% | 18.5% | 48.1%$^B$ |
| #6 (geno #2: KE64: treated charcoal in media, no charcoal in cavity) | 9.3%$^{AB}$ | 29.6%$^A$ | 38.9% | 9.3% | 48.1%$^B$ |

$^1$Means followed by the same letter not significantly different.
$^2$Root in air is a negative result and indicates that the root has lost its geotropism.

TABLE 12

Normalcy Scores for all Treatments

| Treatment | Normal $\alpha = 0.0001^1$ | Would be normal if fully extracted $\alpha = 0.1665$ | Total Germination (Columns 1 + 2) | Unchanged (no germination) $\alpha = 0.0273$ | Not normal $\alpha = 0.1174$ |
|---|---|---|---|---|---|
| #1 (geno#1/#2: KE64: treated charcoal in media and cavity) | 0.0%$^C$ | 13.0% | 13.0% | 38.9% | 37.0% |
| #2 (geno#1: MS09: non-treated charcoal in media, treated charcoal in cavity) | 9.3%$^{BC}$ | 25.9% | 35.2% | 27.8% | 35.2% |
| #3 (geno#1/#2: KE64: treated charcoal in media, treated charcoal in cavity) | 1.9%$^C$ | 9.3% | 11.2% | 33.3% | 55.6% |
| #4 (geno#2: MS09: non-treated charcoal in media, treated charcoal in cavity) | 1.9%$^C$ | 18.5% | 20.4% | 31.5% | 42.6% |
| #5 (geno #1: KE64: treated charcoal in media, no charcoal in cavity) | 16.7%$^A$ | 22.2% | 38.9% | 46.3% | 14.8% |
| #6 (geno #2: KE64: treated charcoal in media, no charcoal in cavity) | 25.9%$^A$ | 22.2% | 48.1% | 33.3% | 16.7% |

$^1$Means followed by the same letter not significantly different.

Discussion of Results:

As shown above in Tables 10-12, there is an increase in germination frequency and organ size of the germinates from manufactured seeds containing the modified nutritive media MS09 with non-nutrient-treated media as compared to manufactured seeds containing KE64 media with nutrient-treated media. Nutrient loading of charcoal is a complex and time-consuming process. Therefore, the use of the modified media MS09 with non-nutrient-treated media provides an important advance in the preparation of manufactured seeds and methods of germinating plant embryos.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing an improved nutritive medium comprising an adsorbent material for culturing plant cells, the method comprising:
   (a) determining whether there is a decrease in the concentration of one or more components in a first nutritive media after incubation with a desired amount of adsorbent material; and
   (b) producing an improved nutritive medium comprising the same components as the first nutritive medium, wherein the improved nutritive medium comprises:
      (i) an increased concentration of the one or more components that was determined in step (a) to decrease in concentration in the presence of the absorbent material; and
      (ii) the same type of absorbent material at a concentration range within two-fold of that which was used in accordance with step (a).

2. The method of claim 1, wherein the adsorbent material is charcoal.

3. The method of claim 2, wherein the concentration of charcoal to be added to the improved nutritive medium is from about 1 g/L to about 100 g/L.

4. The method of claim 2, wherein the charcoal is non-nutrient-treated prior to addition to the nutritive media.

5. The method of claim 2, wherein the nutritive media is for growth of conifer cells.

6. The method of claim 1, wherein the improved nutritive medium comprises at least 2 components selected from the group consisting of $NH_4NO_3$, $KH_2PO_4$, $MgSO_4$, $FeSO_4$, Myo-inositol, Thiamine-HCL, Pyridoxine-HCL, Nicotinic Acid, Riboflavin, Ca-pantothenate, Biotin and Folic Acid, DL-serine, L-proline, L-arginine-HCL and L-alanine.

7. The method of claim 1, further comprising disposing the first nutritive medium of step (a) into a first set of manufactured seeds and disposing the improved nutritive medium of step (b) into a second set of manufactured seeds, placing a conifer embryo into functional contact with the nutritive media in each of the manufactured seeds from the first and second set of manufactured seeds, placing the manufactured seeds into an environment conducive for plant growth and comparing the germination frequencies of the embryos from the first and second set of manufactured seeds.

8. A method for producing an improved nutritive medium comprising an adsorbent material for culturing plant cells, the method comprising:
(a) incubating a first nutritive media comprising a pre-determined initial concentration of components comprising one or more carbon sources, vitamins, minerals and amino acids with a desired amount of adsorbent material to be added to an improved nutritive media;
(b) determining whether there is a decrease in the concentration of one or more of the components in the first nutritive media after the incubation according to step (a) as compared to the pre-determined initial concentration of the component; and
(c) producing an improved nutritive medium comprising the same components as the first nutritive medium, wherein the improved nutritive medium comprises:
(i) an increased concentration of the one or more components that was determined in step (b) to decrease in concentration in the presence of the absorbent material; and
(ii) the same type of absorbent material at a concentration range within two-fold of that which was used in accordance with step (a).

9. The method of claim 8, wherein the first nutritive media is incubated with the absorbent material for a time period of at least 10 minutes up to a week.

10. The method of claim 8, wherein the adsorbent material is charcoal.

11. The method of claim 10, wherein the concentration of charcoal to be added to the improved nutritive medium is from about 1 g/L to about 100 g/L.

12. The method of claim 10, wherein the charcoal is non-nutrient-treated prior to addition to the nutritive media.

13. The method of claim 8, wherein the nutritive media is for growth of conifer cells.

14. The method of claim 8, wherein the nutritive medium comprises at least 2 components selected from the group consisting of $NH_4NO_3$, $KH_2PO_4$, $MgSO_4$, FeSO4, Myo-inositol, Thiamine-HCL, Pyridoxine-HCL, Nicotinic Acid, Riboflavin, Ca-pantothenate, Biotin and Folic Acid, DL-serine, L-proline, L-arginine-HCL and L-alanine.

15. The method of claim 8, wherein the volume of nutritive medium incubated in step (a) is ¼ to ¹⁄₁₀₀₀ the volume of the improved nutritive medium of step (c).

16. The method of claim 8, further comprising disposing the improved nutritive medium of step (c) into one or more manufactured seeds.

17. The method of claim 16, further comprising placing a conifer embryo into functional contact with the nutritive media in the manufactured seed.

18. The method of claim 8, further comprising disposing the first nutritive medium of step (a) into a first set of manufactured seeds and disposing the improved nutritive medium of step (c) into a second set of manufactured seeds, placing a conifer embryo into functional contact with the nutritive media in each of the manufactured seeds from the first and second set of manufactured seeds, placing the manufactured seeds into an environment conducive for plant growth and comparing the germination frequencies of the embryos from the first and second set of manufactured seeds.

* * * * *